United States Patent [19]

Gestaut et al.

[11] 4,448,886

[45] May 15, 1984

[54] BIODISPERSIONS

[75] Inventors: Lawrence J. Gestaut, Concord, Ohio; P. David Simcox, Langhorne, Pa.

[73] Assignee: Diamond Shamrock Corporation, Dallas, Tex.

[21] Appl. No.: 325,652

[22] Filed: Nov. 30, 1981

[51] Int. Cl.³ .................. C12P 3/00; C22B 11/00; C22B 3/00; C25B 11/08
[52] U.S. Cl. .................. 435/262; 435/168; 435/41; 75/118 R; 75/108; 204/294; 423/22; 423/DIG. 17; 502/101
[58] Field of Search ........... 435/168, 262, 41, 243; 423/22, DIG. 17; 75/101 BE, 108, 109, 118 R; 252/425.3; 204/291, 292, 294

[56] References Cited

U.S. PATENT DOCUMENTS

| | | | |
|---|---|---|---|
| 3,212,930 | 10/1965 | Thompson et al. | 204/294 |
| 3,284,332 | 11/1966 | Gladrow et al. | 204/294 |
| 3,580,824 | 5/1971 | Currey et al. | 204/294 |
| 3,850,764 | 11/1974 | Herczog et al. | 204/294 |
| 4,033,763 | 7/1977 | Markels, Jr. | 75/118 R |
| 4,033,765 | 7/1977 | Gerlach | 75/108 |
| 4,046,654 | 9/1977 | Cole | 204/294 |
| 4,095,975 | 6/1978 | Rapps et al. | 75/108 |
| 4,103,073 | 7/1978 | McAlean et al. | 428/474 |
| 4,137,373 | 1/1979 | Jalan et al. | 252/425.3 |
| 4,293,333 | 10/1981 | Drobot | 75/101 BE |
| 4,293,334 | 10/1981 | Drobot et al. | 75/101 BE |
| 4,357,224 | 11/1982 | Hardman et al. | 204/294 |
| 4,357,262 | 11/1982 | Solomon | 204/294 |
| 4,360,380 | 11/1982 | Zarur | 75/118 R |

FOREIGN PATENT DOCUMENTS 95313 1/1973 German Democratic Rep. .
393268 11/1974 Spain .

OTHER PUBLICATIONS

Beveridge et al., "Uptake and Retention of Metals by Cell Walls of Bacillus Subtilis", Journal of Bacteriology 127(1) (1976) pp. 1502–1518.
Tornabene et al, "Microbial Uptake of Lead" Science 176 (1972) pp. 1334–1335.
Water and Wastewater Engineering, vol. 2, Water Purification and Wastewater Treatment and Disposal, Fair, Geyer and Okun, John Wiley & Sons (1968), pp. 34-1–34-11.
Elements of Water Supply and Wastewater Disposal, 2d ed., Fair, Geyer and Okun, John Wiley & Sons (1971), pp. 525–535.
Water-1976 II Biological Waste Water Treatment, Bennett Editor, 167, vol. 73 (1977).
Environmental Biogeochemistry and Geomicrobiology, Proceedings of the International Symposium on Environmental Biogeochemistry, 3rd, Wolfenbuettel, Germany (1977), pp. 975–987 (1978).

*Primary Examiner*—Alvin E. Tanenholtz
*Assistant Examiner*—John E. Tarcza
*Attorney, Agent, or Firm*—Arthur S. Collins; Bruce E. Harang

[57] ABSTRACT

A process for producing high dispersion metal crystallites dispersed substantially homogeneously in a carbonaceous material matrix is disclosed. The novel metal crystallite dispersions disclosed herein have the added advantage of being locked into the matrix thereby preventing migration of the metal crystallites.

11 Claims, No Drawings

BIODISPERSIONS

BACKGROUND OF THE INVENTION

This invention relates to metal crystallites disposed in a carbonaceous material matrix and more particularly to metal crystallites disposed in a carbonaceous matrix prepared by growing microbes in a metal ion or metal ion complex rich environment, harvesting said microbes containing said metal and pyrolizing.

In applications such as elecrodes for chlorine/alkali cells, batteries and fuel cells, it is often desirable to utilize high surface area platinum powder supported on carbon as part of the electrode active layer. In the past, these types of applications used platinum crystallites in the 20 angstrom size region on a carbon support but were only metastable due to the sinterng processes necessary to make these types of materials.

Other metal crystallites have also been found to be beneficial because of their large surface area for other types of electrodes in addition to the platinum carbon electrodes described hereinabove.

In a related area, it is known to remove metal contaminants from a process waste stream by using absorption into living organisms, namely plants, as is described, for example, in *Water Purification and Waste Water Treatment Disposal*, Fair, Geyer and Okun, John Wiley & Sons, 1968; *Elements of Water Supply and Waste Water Disposal*, second edition, Fair, Geyer and Okun, 1971; and *Water-1976 II Biological Waste Water Treatment*, Bennett editor, 167 volume 73, 1977. However, all of these technologies dealing with absorbing the metal in process waste streams do not deal with the recovery and utilization as high dispersion metal crystallites supported in a carbonaceous material matrix. Thus, they do not move forward to the point where applicants' present invention lies.

East German Pat. No. 95,313 issued Jan. 20, 1973, to Horst Steppan describes a method of using a microorganism to deposit a metal on an object by biological-fermentation (i.e., by biologic oxidation and reduction). The metallization is done on the container walls and/or on an object suspended in the fermentation bath. There is no teaching or even speculation on how to provide metallic particles homogeneously suspended in a carbonaceous material matrix while preventing oxidation of the metal ions.

Likewise, the recovery of precious metals out of process waste streams via incorporation into living organisms and then pyrolizing to provide metallic precious metal dispersed in a carbonaceous material has not previously been described in the art. Generally these recoveries have been done via electrowinning such as taught, for example, in U.S. Pat. Nos. 4,095,975 and 4,033,765. Alternatively cation exchange resins have been used to recover these precious metals in process waste streams.

SUMMARY OF THE INVENTION

It has now been found that a high dispersion metal crystallites dispersed substantially homogeneously in a carbonaceous material matrix can be produced utilizing the process of (a) introducing living microbes into a growth medium comprising: a microbe nutrient, liquid solvent and a metal (or metals) in solvated form; (b) growing or respiring said microbes of (a) in said growth medium of (a), allowing said microbes to incorporate said solvated metal or metals; (c) harvesting said microbes containing said metal or metals; and (d) pyrolizing said harvested microbes of (c) in an inert or reducing atmosphere. The high dispersion metal crystallites so produced are superior in their stability against surface area loss and are of high surface area having a size of from less than 20 angstroms to about 200 angstroms or more.

DETAILED DESCRIPTION

LIVING MICROBES

As used herein and hereafter, the term "living microbes" includes single and simple multi-cellular plants and animals. Thus, for example, suitable single cell plants and/or animals are such things as yeasts specifically, for example, Baker's Yeast; fungi, such as, for example, Rhizopus, Fusarium and Neurosora; bacteria such as, for example, Bacillium gram (+), Escherichia coli gram (−); algae such as Euglena and Porphoridium; and protozoa such as, for example, paramecium, didinium, ameoba and vorticella. Also suitable are higher plants including both broadleaf and grasses. Suitable examples are, for example, crabgrass and mung beans. It will be also understood that these living microbes may be anaerobic or aerobic. Further, it is understood that while any one living microbe may be used alone, they also may be used in combination and that some combinations may be advantageous.

The living microbe or microbes selected for any particular use are selected because of their ability to incorporate the solvated metal or metals of interest into their systems. In some cases, the environment may be tailored to them, but in others such as process waste streams, the environment may be dictated by the process.

The living microbes can be added to the nutrient solution, to the metal ion containing solution or separately suspended in a liquid before addition to either or both of the above.

MICROBE NUTRIENT

As used herein and hereafter, "microbe nutrient" includes any material which the living microbes of interest can ingest to sustain their life and to cause proliferation of their species. Typical nutrients include sugars, agar, protein digests, vitamins and salts. It will be further appreciated that the microbe nutrients generally are in a solution form as opposed to solid form when actually in use and that the solution of nutrient may be used alone or may be used with additional liquid solvent. In some cases, the dissolution of the nutrients into the solution containing the solvated metal or metals may be the method of choice, i.e., in a process stream, and the order and manner are not critical to the present invention.

LIQUID SOLVENT

In some instances, amounts of liquid solvent above those commonly used to produce microbe nutrients may be advantageous. Also in some instances, liquid solvents other than used to dissolve the microbe nutrients may be necessary to provide the metal or metals of interest in a solvated form so that they may be absorbed by the living microbes. Thus, for example, an aqueous 0.01 M HCl solution may be added to help ensure metal in the ionic state. Suitable liquid solvents include, for example, water, dilute aqueous solutions containing mineral acids, organic acids, alcohols, oils and mixtures thereof, indeed any solvent capable of supporting the particular microbe life. It is understood that additional solvent, if any, may or may not contain the solvated metal or metals of interest. It is further understood that for most systems liquid slvents other than water are generally minor components as they tend to inhibit or stop microbe growth.

METALS

It is not critical to the present invention as to the starting form of the metal or metals of interest. The criteria is that they are capable of being solvated. Further, in the solvated state it is not critical that the metal or metals be in ionic form. Thus, in some cases, neutral organo complexes containing the metal of interest are useful and/or preferred (for example heme or similar complexes).

In most cases, the solvated metal or metals of interest will be supplied by dissolving a salt or salts of said metal or metals in the solution of microbe nutrient. Thus, for example, chloroplatinic acid may be dissolved in a solution of sugar and water to provide the platinum ions for yeast cells to absorb. Any metal salt which is soluble in the microbe nutrient solution and/or microbe nutrient solution plus liquid solvent can be used in the present invention. Examples of solvated metals or solvated complex metals which are suitable include solvated forms of platinum, rhodium, copper, iron, zinc, cobalt, gold, silver and mixtures thereof. Ruthenium is also excellent, as illustrated in Example 3 herein. Suitable examples of soluble salts include chloroplatinic acid, cis-diammine-dichloroplatinum (II), metal halides and metal chalcogenide.

It is further understood that in the embodiment where the invention is used to process the metals from a process waste stream, the metals are either already in solvated form in the waste stream or are in a form which may be readily made soluble in the waste stream. Examples of waste streams in which the present invention may be used include, for example, waste streams containing silver ions, gold complex ions and platinum complex ions.

Further, the metal or metals can be either dissolved in the nutrient solution or may be separately dissolved and the resulting solvated metal containing solution added to the nutrient solution. Obviously in some cases, the nutrient can be dissolved in the solvated metal containing solution as the order is not critical.

RESPIRING AND HARVESTING

The manner of respiring and the respiring process are not critical to the present invention per se. It will be understood that methods and processes of respiring generally known in the art for a particular microbe or type of microbe will work in the present invention. The method of choice, therefore, will be determined by the microbe being used. Thus, for example, use of incubators, agitation, aeration and the like may be used as is generally taught in the art. Examples of these techniques are shown in the examples below.

The manner of harvesting and the harvesting process are not critical to the present invention. Any of the generally known harvestng methods for the specific microbes used in any instance is acceptable for use in the instant invention. Presently preferred is the filtering of the microbes out of the nutrient solution and washing with distilled water to free the living microbes from the nutrient solution.

PYROLYZING

Generally known methods of pyrolyzing organic materials are suitable for use in the present invention. The pyrolyzing technique used is not critical to the invention. The pyrolyzing should take place in an inert or reducing atmosphere, however, to insure that the metal crystallites produced are in the metallic state as opposed to the oxide state and also to limit the loss of carbonaceous material. Thus, for example, atmospheres such as nitrogen, argon, hydrogen and mixtures thereof are particularly preferred. Other inert and/or reducing atmospheres are suitable and may be used in the present invention. Presently the most useful temperature ranges for pyrolyzing are in the range of 300° to about 1200° C. It will be appreciated that the particular temperature and time utilized are dependent upon the metallic element to be recovered as well as the type of microbe used in the process of the present invention as well as the final size of the metal crystallites so produced.

The invention is illustrated below in the examples, where all percentages are weight percentages unless otherwise noted.

EXAMPLE 1

50 grams of frozen bakers yeast cells were suspended in 200 ml of deionized water. This suspension was added to 200 ml of one percent (weight/weight) sucrose solution containing 1000 ppm chloroplatinic acid. The resultant solution/suspension was agitated for 3 days at room temperature. The yeast were then filtered, resuspended in deionized water, refiltered, pyrolyzed for one hour at 400° C. under nitrogen gas, and finally pyrolyzed in air for 1¾ hours at 400° C. The carbonaceous material so formed was found, by surface determination via gaseous adsorption (BET measurement), to have a surface area of 186 g/m$^2$. A sample was then examined by transmission electron-microscopy (TEM). The results of this analysis by TEM showed platinum crystallites in the metallic state substantially homogeneously disposed throughout the carbonaceous material. A large portion of these crystallites had a size in the range of from approximately 40 to about 50 angstroms.

This example shows the process of producing these metallic crystallites of high dispersion and the fact that they are disposed throughout the carbonaceous material matrix which will tend to lock them in place and keep them from migrating which has been a problem in the art of high dispersion metal crystallite catalytic materials.

EXAMPLE 2

Active yeast cells were prepared by preparing a 6-liter aqueous solution containing 360 g dextrose, 30 g peptone and 30 g of yeast extract mixing and then autoclaving to sterilize the solution. 2 g of dry yeast was added to a 750 ml aliquot of the above sterile solution and agitated overnight at 25° C. in an incubator. The resulting yeast suspension was removed from the incubator and centrifuged for 10 minutes at 3000 rpm in a Beckman R2-65B ultracentrifuge and the liquid media was then decanted off. The yeast was resuspended in 500 ml of 50 mM sucrose solution in a 1-liter flask to which 77 mg of cis-[Pt(NH$_3$)$_2$Cl$_2$] was added. The resultant solution/suspension was agitated overnight at 25° C. The yeast were then centrifuged, resuspended in 25 ml of deionized water and then lyophilized overnight. The resulting material was pyrolyzed at 300° C.

for one hour in an $N_2$ atmosphere and then for ½ hour at 300° C. in an air atmosphere. A sample was then examined by TEM which revealed platinum crystallites in the metallic state substantially homogeneously disposed throughout a carbonaceous material.

EXAMPLE 3

Following the procedure of Example 2, the following metal containing materials were used in place of cis-[Pt(NH$_3$)$_2$Cl$_2$] in the amounts shown in Table I below. In each case, TEM revealed the sample to contain the appropriate metal as a metallic state crystallite substantially homogeneously disposed throughout a carbonaceous material.

TABLE I

| Sample No. | Compound Used | Amount of Metal Compound Introduced | |
|---|---|---|---|
| | | (mg) | (ml of 20% soln) |
| 3A | H$_2$PtCl$_6$ | 133 | — |
| 3B | AuCl$_4$ | 102 | — |
| 3C | RuCl$_3$ | 128 | — |
| 3D | H$_2$Pt(SO$_3$)$_2$OH | — | 0.25 |

EXAMPLE 4 (Comparison)

In this example, the procedure of Example 2 was followed with no metal added. TEM revealed the same type of carbonaceous material as in Examples 1-3 but no metallic crystallites were present indicating clearly that the metal crystallites were produced by the present invention and not by some other mechanism.

While there has been shown and described what is believed, at present, to constitute the preferred embodiments of the present invention, it will be obvious to those skilled in the art that various changes and modifications may be made therein without departing from the scope of the invention as defined by the appended claims.

What is claimed is:

1. A process for producing high dispersion metal crystallites dispersed substantially homogeneously in a carbonaceous material matrix comprising:
   a. introducing living microbes into a growth medium consisting essentially of a microbe nutrient, an aqueous liquid, and at least one metal in solvated form;
   b. growing said microbes in said growth medium, allowing said microbes to incorporate said metal;
   c. harvesting said microbes containing said metal; and
   d. pyrolyzing said harvested, metal-containing microbes in an inert or reducing atmosphere at a temperature of at least about 300° C. thereby yielding said high dispersion metal crystallites dispersed substantially homogeneously in a carbonaceous material matrix coformed therewith during this pyrolysis step.

2. A process as claimed in claim 1 wherein said living microbes are selected from the group consisting of yeast, fungi, algae, protozoa, bacteria and mixtures thereof.

3. A process as claimed in claim 1 wherein said microbe nutrient is selected from the group consisting of sugars, agar, protein digests, vitamins, salts and mixtures thereof.

4. A process as claimed in claim 1 wherein said aqueous liquid is selected from the group consisting of water, dilute aqueous solutions containing mineral acids, organic acids, alcohols, oils and mixtures thereof, further characterized in that said microbes can live in said aqueous liquid.

5. A process as claimed in claim 1 wherein said metal in solvated form is provided by using a soluble salt or salts of said metal.

6. A process as claimed in claim 1 wherein said metal in solvated form is from the group consisting of ruthenium platinum, rhodium, copper, zinc, iron, cobalt, gold, and silver.

7. A process as claimed in claim 1 wherein said step (d) is carried out at a temperature of from about 300° to about 1200° C. in an atmosphere selected from the group consisting of nitrogen, argon, hydrogen and mixtures thereof.

8. A process as claimed in claim 1 wherein said metal is a noble or precious metal.

9. A process as in claim 8 wherein said metal is ruthenium.

10. A process for producing high dispersion platinum crystallites dispersed substantially homogeneously in a carbonaceous material matrix comprising:
    a. introducing living microbes into a growth medium consisting essentially of a microbe nutrient, an aqueous liquid, and platinum in solvated form;
    b. growing said microbes in said growth medium, allowing said microbes to incorporate said platinum;
    c. harvesting said microbes containing said platinum; and
    d. pyrolyzing said harvested, platinum-containing microbes in an inert or reducing atmosphere at a temperature of at least about 300° C. thereby yielding said high dispersion platinum crystallites dispersed substantially homogeneously in a carbonaceous material matrix coformed therewith during this pyrolysis step.

11. A process as claimed in claim 10 wherein said platinum in solvated form is provided by using chloroplatinic acid.

* * * * *